United States Patent [19]

Jautelat et al.

[11] Patent Number: 5,122,532
[45] Date of Patent: Jun. 16, 1992

[54] MICROBICIDAL HALOGENOALLYL-AZOLYL DERIVATIVES

[75] Inventors: Manfred Jautelat, Burscheid; Klaus Stroech, Solingen; Gerd Hänssler, Leverkusen; Stefan Dutzmann, Hilden; Karl-Heinz Kuck, Langenfeld; Wilhelm Brandes, Leichlingen, all of Fed. Rep. of Germany

[73] Assignee: Bayer Aktiengesellschaft, Leverkusen, Fed. Rep. of Germany

[21] Appl. No.: 645,936

[22] Filed: Jan. 25, 1991

[30] Foreign Application Priority Data

Feb. 3, 1990 [DE] Fed. Rep. of Germany ....... 4003181

[51] Int. Cl.$^5$ ................. A01N 43/653; C07D 249/08
[52] U.S. Cl. ................... 514/383; 514/184; 548/101; 548/267.8; 548/268.6
[58] Field of Search .............. 548/101, 267.8, 268.6; 514/184, 383

[56] References Cited

U.S. PATENT DOCUMENTS 4,655,820 4/1987 Worthington ............................ 71/92
4,871,389 10/1989 Elliott et al. ............................ 71/92

Primary Examiner—Patricia L. Morris
Attorney, Agent, or Firm—Sprung Horn Kramer & Woods

[57] ABSTRACT

A microbicidal halogenoallyl-azolyl derivatives of the formula $$X^1-C(X^3)=C(X^2)-CH_2-C(OR^2)(R^1)-CH_2-\text{azolyl} \quad (I)$$

in which
R$^1$ represents halogenoallyl, propargyl, substituted cycloalkyl or optionally substituted heteroaryl, or represents a radical of the formula $$-C(CH_2R_4)(CH_3)-CH_2-R^3 \quad \text{or} \quad -C(CH_3)(CH_3)-R^5$$

where
R$^3$ represents hydrogen, halogen, or phenyl which is optionally substituted by halogen, phenoxy which is optionally substituted by halogen or phenoxymethyl which is optionally substituted by halogen,
R$^4$ represents hydrogen or halogen, and
R$^5$ represents iso-propyl, or phenyl which is optionally substituted by halogen or phenoxy which is optionally substituted by halogen or phenoxy which is optionally substituted by halogen,
R$^2$ represents hydrogen, alkyl, alkenyl, acyl or aralkyl,
X$^1$ represents halogen,
X$^2$ represents halogen,
X$^3$ represents hydrogen or halogen and
Y represents nitrogen or a CH group, and addition products thereof with acids and metal salts.

8 Claims, No Drawings

MICROBICIDAL HALOGENOALLYL-AZOLYL DERIVATIVES

The present invention relates to new halogenoallyl-azolyl derivatives, to a plurality of processes for their preparation, and to their use as microbicides in plant protection and in the protection of materials.

It has been disclosed that certain dihalogenoallyl-triazolyl derivatives have fungicidal properties (cf. EP-OS (European Published Specification) 0,097,425). For example, 4-(2,4-dichloro-phenyl)-1,2-dibromo-4-hydroxy-5-(1,2,4-triazol-1-yl)-pent-1-ene and 4-(2,4-dichloro-phenyl)-1,2-dichloro-4-hydroxy-5-(1,2,4-triazol-yl)-pent-1-ene for combating fungi. The action of these substances is good, but leaves something to be desired in some cases when low amounts are applied.

New halogenoallyl-azolyl derivatives of the formula

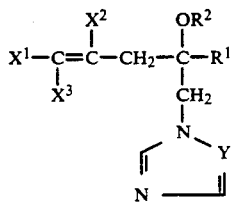

in which
R$^1$ represents halogenoallyl, propargyl, substituted cycloalkyl or optionally substituted heteroaryl, or represents the radicals of the formulae

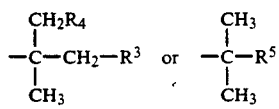

where
R$^3$ represents hydrogen, halogen, or phenyl which is optionally substituted by halogen, phenoxy which is optionally substituted by halogen or phenoxymethyl which is optionally substituted by halogen,
R$^4$ represents hydrogen or halogen, and
R$^5$ represents iso-propyl, or phenyl which is optionally substituted by halogen or phenoxy which is optionally substituted by halogen,
R$^2$ represents hydrogen, alkyl, alkenyl, acyl or aralkyl,
X$^1$ represents halogen,
X$^2$ represents halogen,
X$^3$ represents hydrogen or halogen and
Y represents nitrogen or a CH group, and their acid addition salts and metal salt complexes have now been found.

The compounds of the formula (I) contain an asymmetrically substituted carbon atom and can therefore be obtained in the two optical isomer forms. Moreover, the substances of the formula (I) can be present in two geometric isomer forms, depending on the position of the halogen atoms at the double bond. The present invention relates to the isomer mixtures as well as the individual isomers.

It has furthermore been found that halogenoallylazolyl derivatives of the formula (I) and their acid addition salts and metal salt complexes are obtained when
a) alkynes of the formula

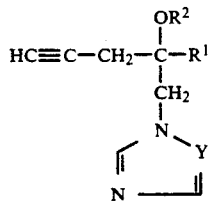

in which
R$^1$, R$^2$ and Y have the abovementioned meanings, are reacted with halogen or halogen-donating compounds in the presence of a diluent, or
b) alkenes of the formula

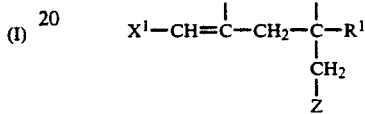

in which
R$^1$, R$^2$, X$^1$ and X$^2$ have the abovementioned meanings and Z represents halogen, alkylsulphonate or arylsulphonate,
are reacted with azoles of the formula

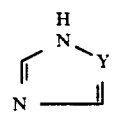

in which
Y has the abovementioned meaning, in the presence of an acid-binding agent and in the presence of a diluent,
or
c) alkynes of the formula

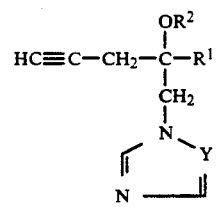

in which
R$^1$, R$^2$ and Y have the abovementioned meanings, are reacted, in a first step, with hypohalites of the formula $$MOX^4 \qquad (V)$$

in which
M represents alkali metal and
X$^4$ represents halogen, in the presence of a diluent, and, in a second step, the resulting halogenoalkynes of the formula

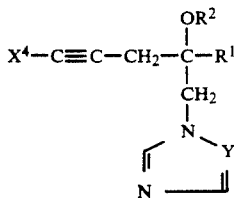

in which

R¹, R², X⁴ and Y have the abovementioned meanings, are reacted with halogen or halogen-donating compounds in the presence of a diluent, and, if appropriate, an acid or a metal salt is subsequently added on to the resulting compounds of the formula (I).

Finally, it has been found that the new halogenoallylazolyl derivatives of the formula (I) and their acid addition salts and metal salt complexes have powerful microbicidal properties and can be employed in plant protection as well in the protection of materials.

Surprisingly, the substances according to the invention have a better microbicidal activity, in plant protection and in the protection of materials, than the previously known compounds which have the most similar structure and the same direction of action.

Formula (I) provides a general definition of the halogenoallyl-azolyl derivatives according to the invention. Preferred compounds of the formula (I) are those in which R¹ represents allyl which is monosubstituted to trisubstituted by fluorine, chlorine and/or bromine, or represents propargyl, or represents cycloalkyl which has 3 to 7 carbon atoms, each of these cycloalkyl radicals being monosubstituted to trisubstituted by identical or different substituents, the substituents being alkyl having 1 to 4 carbon atoms and/or halogen, or R¹ represents a five- or six-membered heteroaromatic radical which has 1 to 3 hetero atoms such as nitrogen, sulphur and/or oxygen, and which is optionally benzo-fused, each of these radicals being optionally monosubstituted to trisubstituted by identical or different substituents, the substituents being halogen, alkyl having 1 to 4 carbon atoms, hydroxyalkyl having 1 to 4 carbon atoms, hydroxyalkinyl having 3 to 8 carbon atoms, alkoxy having 1 to 2 carbon atoms, alkylthio having 1 or 2 carbon atoms, halogenoalkyl, halogenoalkoxy and halogenoalkylthio, each of which has 1 or 2 carbon atoms and 1 to 5 identical or different halogen atoms such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and/or cyano, or R¹ represents the radicals of the formulae

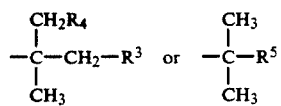

where

R³ represents hydrogen, fluorine, chlorine, bromine, or phenyl which is optionally monosubstituted to trisubstituted by identical or different substituents, the substituents being fluorine, chlorine and/or bromine, or represents phenoxy which is optionally monosubstituted to trisubstituted by identical or different substituents, the substituents being fluorine, chlorine and/or bromine, or represents phenoxymethyl which is optionally monosubstituted to trisubstituted by identical or different substituents, the substituents being fluorine, chorine and/or bromine, R⁴ represents hydrogen, fluorine, chlorine or bromine and R⁵ represents iso-propyl, or represents phenyl which is optionally monosubstituted to trisubstituted by identical or different substituents, the substituents being fluorine, chlorine and/or bromine, or represents phenoxy which is optionally monosubstituted to trisubstituted by identical or different substituents, the substituents being fluorine, chlorine and/or bromine, R² represents hydrogen, alkyl having 1 to 6 carbon atoms, alkenyl having 3 to 6 carbon atoms, acyl having 1 to 4 carbon atoms or phenylalkyl having 1 to 4 carbon atoms in the alkyl moiety, X¹ represents fluorine, chlorine, bromine or iodine, X² represents fluorine, chlorine, bromine or iodine, X³ represents hydrogen, chlorine, bromine or iodine, and Y represents a nitrogen atom or a CH group.

Particularly preferred compounds of the formula (I) are those in which

R¹ represents allyl which is monosubstituted to trisubstituted by fluorine, chlorine and/or bromine, or represents propargyl or represents cycloalkyl having 3 to 6 carbon atoms, each of these cycloalkyl radicals being monosubstituted or disubstituted by methyl, ethyl, fluorine, chlorine and/or bromine, or R¹ represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, each of these radicals being monosubstituted to trisubstituted by identical or different substituents, the substituents being fluorine, chlorine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkynyl having 4 to 6 carbon atoms, methoxycarbonyl, ethoxycarbonyl, methoxyiminomethyl, 1-methoximino-ethyl, nitro, cyano, formyl, dimethoxymethyl, acetyl and/or propionyl, or R¹ represents the radicals of the formulae

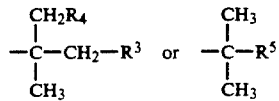

where

R³ represents hydrogen, fluorine, chlorine, phenyl which is optionally monosubstituted or disubstituted by identical or different substituents, the substituents being fluorine and/or chlorine, or phenoxy which is optionally monosubstituted or disubstituted by identical or different substituents, the substituents being fluorine and/or chlorine, or represents phenoxymethyl which is optionally monosubstituted or disubstituted by identical or different substituents, the substituents being fluorine and/or chlorine R⁴ represents hydrogen, fluorine or chlorine, R⁵ represents iso-propyl, or phenyl which is optionally monosubstituted or disubstituted by identical or different substituents, the substituents being fluorine and/or chlorine, or represents phenoxy which is optionally monosubstituted or disubstituted by identical or different substituents, the substituents being fluorine and/or chlorine, R² represents hydrogen, methyl, ethyl, n-propyl, iso-propyl, n-butyl, allyl, formyl, acetyl, benzyl or phenethyl, X¹ represents fluorine, chlorine, bromine or iodine,
X² represents fluorine, chlorine, bromine or iodine,
X³ represents hydrogen, chlorine, bromine or iodine, and Y represents a nitrogen atom or a CH group.

Other preferred compounds according to the invention are addition products of acids and those halogenoallyl-azolyl derivatives of the formula (I) in which R¹, R², X¹, X², X³ and Y have those meanings which have been mentioned as being preferred for these substituents.

The acids which can be added on preferably include hydrohalic acids such as, for example, hydrochloric acid and hydrobromic acid, in particular hydrochloric acid, furthermore phosphoric acid, nitric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid, and also sulphonic acids such as, for example, p-toluenesulphonic acid and 1,5-naphthalenedisulphonic acid.

Other preferred compounds according to the invention are addition products of salts of metals of main group II to IV and subgroup I and II as well as IV to VIII of the Periodic System of the Elements and those halogenoallyl-azolyl derivatives of the formula (I) in which R¹, R², X¹, X³ and Y have those meanings which have been mentioned as being preferred for these substituents.

In this context, salts of copper, zinc, manganese, magnesium, tin, iron and of nickel are particularly preferred. Suitable anions of these salts are those which are derived from those acids which lead to physiologically acceptable addition products. Acids of this type which are particularly preferred in this connection are the hydrohalic acids such as, for example, hydrochloric acid and hydrobromic acid, furthermore phosphoric acid, nitric acid and sulphuric acid.

Examples which may be mentioned of substances according to the invention are the halogenoallyl-azolyl derivatives mentioned in the table below.

TABLE 1

$$X^1-C(X^3)=C(X^2)-CH_2-C(OR^2)(R^1)-CH_2-N\langle\text{azolyl}\rangle\text{Y} \quad (I)$$

| X¹ | X² | X³ | R¹ | R² | Y |
|----|----|----|----|----|---|
| I  | I  | H  | —C(CH₃)₃ | H | N |
| F  | F  | H  | —C(CH₃)₃ | H | N |
| I  | I  | H  | —C(CH₃)₃ | H | CH |
| F  | F  | H  | —C(CH₃)₃ | H | CH |
| Cl | Cl | H  | —C(CH₃)₃ | CH₃ | N |
| Cl | Cl | H  | —C(CH₃)₃ | C₂H₅ | N |
| Br | Br | H  | —C(CH₃)₃ | —CH₂—C₆H₅ | N |
| Cl | Cl | H  | —C(CH₃)₃ | —CH₂—C₆H₅ | N |
| Cl | Cl | H  | —C(CH₃)(CH₃)—CH(CH₃)₂ | H | N |
| Cl | Cl | H  | 1-methylcyclohexyl | H | N |
| Cl | Cl | H  | 1-methylcyclobutyl | H | N |
| Cl | Cl | H  | 1-ethylcyclobutyl | H | N |
| Cl | Cl | H  | —C(CH₃)₂—C₆H₅ | H | N |
| Cl | Cl | H  | —C(CH₃)(CH₃)—CH₂F | H | N |
| Cl | Cl | H  | —C(CH₂F)(CH₃)—CH₂F | H | N |
| Cl | Cl | H  | —C(CH₃)(CH₃)—CH₂Cl | H | N |

TABLE 1-continued $$X^1-C(X^3)=C(X^2)-CH_2-C(OR^2)(R^1)-CH_2-N(Y)-N=CH-N \quad (I)$$

| $X^1$ | $X^2$ | $X^3$ | $R^1$ | $R^2$ | Y |
|---|---|---|---|---|---|
| Cl | Cl | H | -C(CH₂Cl)(CH₃)(CH₂Cl) | H | N |
| Cl | Cl | H | -C(CH₃)₂-(4-Cl-C₆H₄) | H | N |
| Cl | Cl | H | -C(CH₃)₂-(2,4-Cl₂-C₆H₃) | H | N |
| Cl | Cl | H | -C(CH₃)₂-(2,4-F₂-C₆H₃) | H | N |
| Cl | Cl | H | 2-thienyl | H | N |
| Cl | Cl | H | 3-thienyl | H | N |
| Cl | Cl | H | 2-furyl | H | N |
| Cl | Cl | H | 2-pyridyl | H | N |
| Cl | Cl | H | -C(CH₃)₂-(4-F-C₆H₄) | H | N |
| Cl | Cl | H | 3-pyridyl | H | N |
| Cl | Cl | H | 1-imidazolyl | H | N |
| Cl | Cl | H | 1-pyrazolyl | H | N |
| Cl | Cl | H | 2-methylquinolin-? (quinolinyl) | H | N |
| Cl | Cl | Cl | -C(CH₃)₃ | CH₃ | N |
| Cl | Br | Br | -C(CH₃)₃ | CH₃ | N |
| Cl | Cl | Cl | -C(CH₃)₂-CH(CH₃)₂ | H | N |
| Cl | Br | Br | -C(CH₃)₂-CH(CH₃)₂ | H | N |
| Cl | Cl | Cl | 1-methylcyclohexyl | H | N |
| Cl | Cl | Cl | -C(CH₃)₂-C₆H₅ | H | N |
| Cl | Cl | Cl | -C(CH₂F)₂-CH₃ | H | N |

If 4-(1-chloro-cyclopropyl)-4-hydroxy-5-(1,2,4-triazol-1-yl)-pent-1-yne is used as starting substance and a solution of chlorine gas in methylene chloride as reactant, the course of process (a) according to the invention can be illustrated by the following equation:

$$HC{\equiv}C-CH_2-\underset{\underset{N\diagdown N{=}CH}{\overset{|}{CH_2}}}{\overset{\overset{OH}{|}}{C}}-\underset{\diagup\diagdown}{C}Cl \xrightarrow{Cl_2 / CH_2Cl_2}$$

-continued

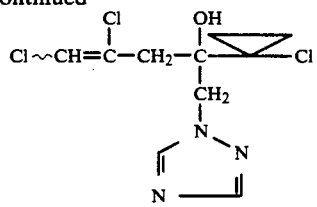

If 1,2-dichloro-4-hydroxy-4-chlormethyl-5,5-dimethyl-hex-1-ene and 1,2,4-triazole are used as starting substances, the course of process (b) according to the invention can be illustrated by the following equation:

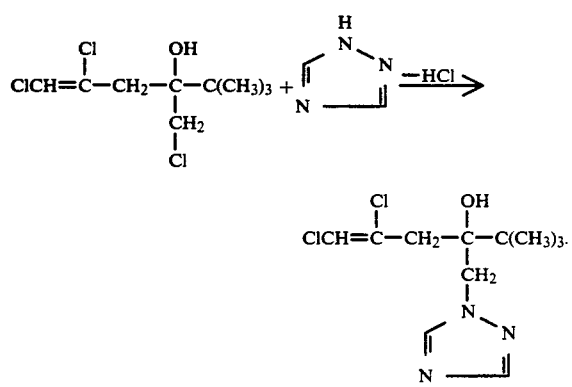

If 4-tert.-butyl-5-(1,2,4-triazol-1-yl)-pent-1-yn-4-ol is used as starting substance and bromine in the presence of potassium hydroxide, and bromine, respectively, are used as reactants, the course of process (c) according to the invention can be illustrated by the following equation:

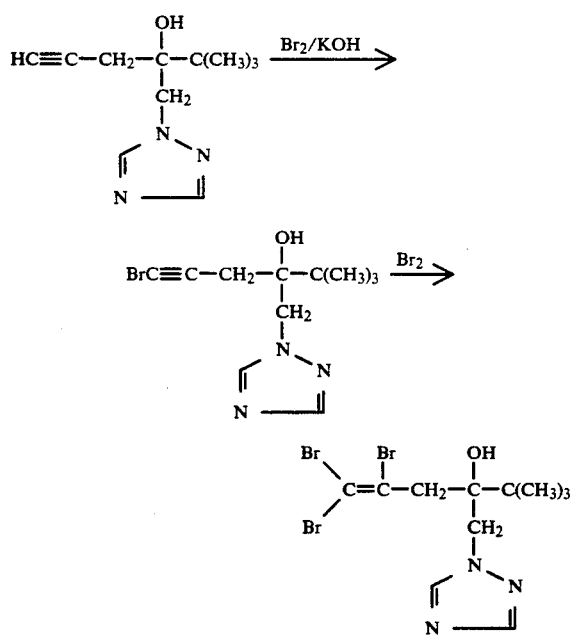

Formula (II) provides a general definition of the alkines required as starting substances when carrying out the process (a) according to the invention. In this formula, $R^1$, $R^2$ and Y preferably have those meanings which have already been mentioned in connection with the description of the substances of the formula (I) according to the invention as being preferred for these radicals.

Some of the alk nes of the formula (II) are known, cf. EP-OS (European Published Specification) 0,096,786). They can be prepared by d) in step one reacting azolyl methyl ketones of the formula

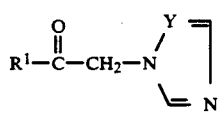   (VII)

in which
R$^1$ and Y have the abovementioned meanings, with propargyl halides of the formula

   (VIII)

in which
Hal represents chlorine or bromine, in the presence of activated aluminum and in the presence of a diluent, and, if appropriate, in step two reacting the alkynes formed in this process of the formula

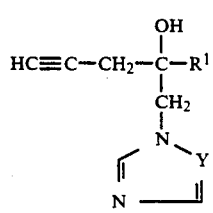   (IIa)

in which
R$^1$ and Y have the abovementioned meanings, with strong bases in the presence of a diluent, and in step three reacting the alcoholates formed in this process, of the formula

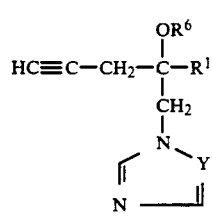   (IIb)

in which
R$^1$ and Y have the abovementioned meanings and R$^6$ represents a cationic radical of a base, with halogen compounds of the formula R$^7$—Hal'   (IX)

in which
R$^7$ represents alkyl, alkenyl, acyl or aralkyl and Hal' represents chlorine, bromine or iodine, in the presence of a diluent, or e) in step one reacting chloromethyl ketones of the formula

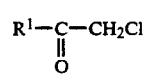   (X)

in which
R¹ has the abovementioned meaning, with propargyl halides of the formula $$HC\equiv C-CH_2-Hal \quad (VIII)$$

in which
Hal has the abovementioned meaning, under the conditions mentioned in step one of process (d), and then in step two reacting the hydroxyalkines formed in this process of the formula $$HC\equiv C-CH_2-\underset{\underset{Cl}{\overset{\displaystyle CH_2}{|}}}{\overset{\displaystyle OH}{\underset{|}{C}}}-R^1 \quad (XII)$$

in which
R¹ has the abovementioned meaning, with azoles of the formula

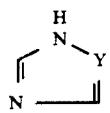

(IV)

in which
Y has the abovementioned meaning, in the presence of an acid-binding agent and in the presence of a diluent, and, if appropriate, in step three further reacting the alkynes formed in this process, of the formula

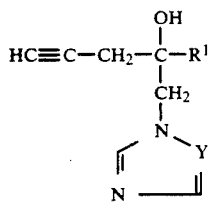

(IIa)

in which
R¹ and Y have the abovementioned meanings, according to process (d).

Formula (VII) provides a general definition of the azolyl methyl ketones required as starting substances when carrying out process (d). In this formula, Y and R¹ preferably have those meanings which have already been mentioned in connection with the description of the substances of the formula (I) according to the invention as being preferred for these radicals.

The azolyl methyl ketones of the formula (VII) are known or can be prepared in a simple manner by processes known in principle (cf. DE-OS (German Published Specification) 2,431,407).

The propargyl halides of the formula (VIII) required as reactants in process (d) are known.

Diluents which can be used when carrying out step one of process (d) are all inert organic solvents which are customary for reactions of this type. Ethers such as tetrahydrofuran or diethyl ether are preferably suitable.

Step one of process (d) is carried out in the presence of activated aluminum. The latter is prepared by adding catalytic amounts of mercury(II) chloride and iodine to aluminum flakes.

When carrying out step one of process (d), the reaction temperatures can be varied within a substantial range. In general, the process is carried out at temperatures between −80° C. and +100° C., preferably at temperatures between −70° C. and +60° C.

Process (d) as well as processes (a), (b), (c) and (e) are generally carried out under atmospheric pressure.

When carrying out step one of process (d), a procedure is generally followed in which 1 to 2 mols of propargyl halide of the formula (VIII) and 1 to 1.5 mols of aluminum and catalytic amounts of mercury(II) chloride and iodine are employed per mol of azolyl methyl ketone of the formula (VII). The products formed are isolated by customary methods.

In step two of process (d), the alkynes of the formula (IIa) are converted into the corresponding alcoholates by reacting them with suitable strong bases such as alkali metal amides or alkali metal hydrides, quaternary ammonium hydroxides or phosphonium hydroxides, in an inert diluent such as, for example, dioxane, at room temperature. R⁶ in the compounds of the formula (IIb) accordingly preferably represents an alkali metal cation such as a sodium or potassium cation, or represents a quaternary ammonium or phosphonium cation.

Formula (IX) provides a general definition of the halogen compounds required as reactants when carrying out step three of process (d). In this formula, R⁷ preferably represents those meanings which have already been mentioned for substituents R² in connection with the description of the substances of the formula (I) according to the invention, with the exception of hydrogen. Hal represents chlorine, bromine or iodine.

The halogen compounds of the formula (IX) are known or can be prepared by methods known in principle.

Suitable diluents for carrying out steps two and three of process (d) are inert organic solvents. Solvents which can preferably be used are ethers such as diethyl ether or dioxane; aromatic hydrocarbons such as benzene; in some cases also chlorinated hydrocarbons such as chloroform, methylene chloride or carbon tetrachloride; and also hexamethylphosphoric triamide.

When carrying out steps two and three of process (d), the reaction temperatures can be varied within a substantial range. The process is generally carried out at temperatures between 0° C. and 120° C., preferably between 20° C. and 100° C.

When carrying out step two of process (d), alkynes of the formula (IIa) are first reacted with strong bases to give the corresponding alcoholates of the formula (IIb). In step three which follows, 1 to 2 mols of halogen compound of the formula (IX) are preferably employed per mol of an alcoholate of the formula (IIb). To isolate the end products, the reaction mixture is freed of solvent, and the residue is treated with water and an organic solvent. The organic phase is separated off, and worked up and purified in a customary manner.

In a preferred embodiment, steps two and three of process (d) are expediently carried out in such a way that, starting with a hydroxy compound of the formula (IIa), the latter is converted into the alkali metal alcoholate in a suitable organic solvent by means of alkali metal hydride or alkali metal amide, and the alkali metal alcoholate is immediately reacted with a halogen compound of the formula (IX), without isolation, the compounds of the formula (II) being obtained in one pass, with the elimination of alkali metal halide.

In a further preferred embodiment, it is expedient to prepare the alcoholates and to react them with a halogen compound of the formula (IX) in a two-phase system such as, for example, aqueous sodium hydroxide solution or potassium hydroxide solution/toluene or methylene chloride, with the addition of 0.01–1 mol of a phase transfer catalyst such as, for example, ammonium or phosphonium compounds, during which process the alcoholates are reacted with the halides in the organic phase at the boundary layer or in the organic phase.

Formula (X) provides a general definition of the chloromethyl ketones required as starting substances when carrying out process (e). In this formula, $R^1$ preferably has those meanings which have already been mentioned in connection with the description of the substances of the formula (I) according to the invention as being preferred for this radical.

The chloromethyl ketones of the formula (X) are known or can be prepared by methods known in principle (cf. DE-OS (German Published Specification) 3,049,461).

Step one of process (e) is carried out under those conditions which are also applied when step one of process (d) is carried out.

The hydroxyalkynes of the formula (XII) can be directly further reacted with azoles of the formula (IV). Alternatively, they can also first converted into oxiranes which are then reacted with azoles of the formula (IV).

Suitable acid-binding agents when carrying out step two of process (e) are all customary acid acceptors. The following can preferably be used: alkali metal carbonates and hydrogen carbonates, such as sodium carbonate, potassium carbonate or sodium hydrogen carbonate, furthermore tertiary aliphatic or aromatic amines such as triethylamine, N,N-dimethyl-cyclohexylamine, N,N-dimethyl-benzylamine and pyridine, and moreover cyclic amines such as 1,5-diaza-bicyclo[4.3.0]non-5-ene (DBN), 1,8-diaza-bicyclo[5.4.0]undec-7-ene (DBU) and 1,4-diaza-bicyclo [2.2.2]octane (DABCO).

Suitable diluents when carrying out step two of process (e) are all inert organic solvents. The following can preferably be used: aliphatic and aromatic, optionally halogenated hydrocarbons such as pentane, hexane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether and also tert-butyl methyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl and ethyl acetate, nitriles such as, for example, acetonitrile and propionitrile, and pyridine.

When carrying out step two of process (e) the reaction temperatures can also be varied within a relatively wide range. In general, the process is carried out at temperatures between 0° C. and 200° C., preferably between 20° C. and 150° C.

When carrying out step two of process (e), a procedure is generally followed in which an equivalent amount or even an excess of azole of the formula (IV) and 2 to 3 mols of acid-binding agent are employed per mol of hydroxyalkine of the formula (XII). Working-up is carried out by customary methods. If desired, the alkynes of the formula (IIa) are further reacted in process (e) in the same manner as in process (d).

Suitable halogens when carrying out process (a) according to the invention are preferably fluorine, chlorine, bromine and iodine as reactants, furthermore mixed halogens such as chlorine(I) fluoride, bromine(I) fluoride, iodine(I) fluoride, bromine(I) chloride, iodine(I) chloride or iodine(I) bromide (see Methodicium Chimicium, F. Korte, Vol. 7, p. 842 (1976)).

Halogen-donating compounds which can be used, are, for example, sulphuryl chloride, N-bromosuccinimide with hydrochloric acid, N-chlorosuccinimide with hydrobromic acid or N-chlorosuccinimide with hydrogen fluoride/pyridine (see Synthesis 1973, 780).

The addition of the halogens onto the alkynes of the formula (II) can be promoted by the action of light, by heat, by radical-forming substances such as organic peroxides, by surface-active substances such as active carbon, or metal salts, such as copper(II) chloride or iron(III) chloride. In some cases, this can be used for influencing the isomer ratio (E/Z) (see Houben-Weyl, Methoden der Org. Chemie [Methods in Org. Chemistry], Vol. V/3, p. 551 (1962)).

Diluents which can be employed when carrying out process (a) according to the invention are all inert organic solvents which are customary for reactions of this type. Halogenated aliphatic hydrocarbons such as methylene chloride, chloroform and carbon tetrachloride can preferably be used.

When carrying out process (a) according to the invention the temperatures can be varied within a certain range. In general, the process is carried out at temperatures between −10° C. and +120° C., preferably between −5° C. and +80° C.

When carrying out process (a) according to the invention, an equivalent amount or an excess of halogen, or halogen-donating compound, is generally employed per mol of alkyne of the formula (II). Working-up is carried out by customary methods. In general, a procedure is followed in which the reaction mixture is diluted with an organic solvent which is sparingly soluble in water, the mixture is washed with water, and the organic phase is dried then concentrated. However, it is also possible to concentrate the reaction mixture when the reaction has ended directly by stripping off the volatile components under reduced pressure. If desired, the products formed can be further purified by customary methods.

Formula (III) provides a general definition of the alkenes required as starting substances in process (b) according to the invention. In this formula, $R^1$, $R^2$, $X^1$ and $X^2$ preferably have those meanings which have already been mentioned in connection with the description of the substances of the formula (I) according to the invention as being preferred for these substances. Z preferably represents chlorine, bromine, iodine, methylsulphonate or p-tolylsulphonate.

The alkenes of the formula (III) can be prepared by customary methods. For example, alkenes of the formula (III) are obtained by reacting hydroxyalkynes of the formula (XII) with halogens in the presence of a diluent. In this case, the reaction conditions correspond to those which are applied in the case of process (a) according to the invention.

Suitable diluents when carrying out process (b) according to the invention are all customary inert organic solvents. Solvents which can preferably be employed are those which have already been mentioned in connection with the description of step two of process (e) as being preferred.

Suitable acid-binding agents when carrying out process (b) according to the invention are all customary acid acceptors. Acid-binding agents which can preferably be used are all those which have already been mentioned in connection with the description of step two of process (e) as being preferred acid acceptors.

When carrying out process (b) according to the invention, the reaction temperatures can be varied within a relatively wide range. In general, the process is carried out at temperatures between 0° C. and 150° C., preferably between 20° C. and 120° C.

When carrying out process (b) according to the invention, a procedure is generally followed in which an equivalent amount or an excess of azole of the formula (IV) and 2 to 3 mols of acid-binding agent are employed per mol of alkene of the formula (III). Working-up is carried out by customary methods.

Formula (V) provides a general definition of the hypohalites required as reactants when carrying out process (c) according to the invention. In this formula, M preferably represents a sodium or potassium ion, and $X^4$ preferably represents chlorine, bromine or iodine. The hypohalite is preferably prepared freshly from base and halogen.

Diluents which can be employed when carrying out process (c) according to the invention are all inert organic solvents customary for reactions of this type, for carrying out step one as well as step two. Halogenated aliphatic hydrocarbons such as methylene chloride, chloroform and carbon tetrachloride can preferably be used.

When carrying out process (c) according to the invention, the temperatures can be varied within a certain range, both in step one and in step two. In general, the process is carried out at temperatures between $-10°$ C. and $+120°$ C., preferably between $-5°$ C. and 80° C.

When carrying out step one of process (c) according to the invention, an excess of hypohalite is generally employed per mol of alkyne of the formula (II). When carrying out step two of process (c) according to the invention, an equivalent amount or an excess of halogen is generally employed per mol of halogenoalkyne of the formula (VI). Working up is carried out by customary methods, in step one as well as in step two.

The halogenoallyl-azolyl derivatives of the formula (I) which can be obtained by the processes according to the invention can be converted into acid addition salts or metal salt complexes.

Suitable acids for preparing acid-addition salts of the compounds of the formula (I) are preferably those which have already been mentioned in connection with the description of the acid addition salts according to the invention as being preferred.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and, if desired, purified by washing with an inert organic solvent.

Suitable salts of metals for preparing metal salt complexes of the compounds of the formula (I) are preferably those which have already been mentioned in connection with the description of the metal salt complexes according to the invention as being preferred.

The metal salt complexes of the compounds of the formula (I) can be obtained in a simple manner by customary methods, thus for example by dissolving the metal salt in alcohol, for example ethanol, and adding the solution to compounds of the formula (I). Metal salt complexes can be isolated in a known manner, for example by filtration, and, if desired, purified by recrystallization.

The active compounds according to the invention have a powerful microbicidal action and can be employed for combating undesired microorganisms such as fungi and bacteria in plant protection and in the protection of materials.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species such as Pseudoperonospora humuli or *Pseudoperonospora cubensis;*
Plasmopara species, such as *Plasmopara viticola;*
Peronospora species, such as *Peronospora pisi* or *P. brassicae;*
Erysiphe species, such as *Erysiphe graminis;*
Sphaerotheca species such as *Sphaerotheca fuliginea;*
Podosphaera species, such as for example, *Podosphaera leucotricha;*
Venturia species, such as *Venturia inaequalis;*
Pyrenophora species, such as *Pyrenophora teres* or *P. graminea;*
(conidia form: Drechslera, syn: Helminthosporium);
Cochliobolus species, such as *Cochliobolus sativus (conidia form: Drechslera, syn: Helminthosporium);*
Uromyces species, such as *Uromyces appendiculatus;*
Puccinia species, such as *Puccinia recondita;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae;*
Pseudocercosporella species such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating cereal and rice diseases, such as Pseudocercosporella, Erysiphe, Fusarium, Pyrenophora, Cochliobolus, Pyricularia and Pellicularia, and for combating mildew on cucumbers and apple scab, and moreover for combating Botrytis in fruit and vegetable growing and in viticulture. Moroever, they have a good and broad in-vitro action and are suitable for combating powdery mildews, such as Rhizoctonia solani.

In the protection of materials, the substances according to the invention can be employed for the protection of industrial materials against attack and destruction by undesired microorganisms.

Industrial materials in the present connection are to be understood as meaning non-live materials which have been prepared for use in industry. For example, industrial materials which are to be protected by active compounds according to the invention from microbial change or destruction can be glues, sizes, paper and board, textiles, leather, wood, paints and plastic articles, cooling lubricants and other materials which can be attacked or decomposed by microorganisms. Parts of production plants, for example cooling-water circuits, which may be impaired by the multiplication of microorganisms may also be mentioned within the scope of the materials to be protected. Industrial materials which may be mentioned within the scope of the present invention are preferably glues, sizes, papers and boards, leather, wood, paints, cooling lubricants and heat-transfer liquids, particularly preferably wood.

Microorganisms, capable of degradation or change of the industrial materials, which may be mentioned are, for example, bacteria, fungi, yeasts, algae and slime organisms. The active compounds according to the invention preferably act against fungi, in particular molds, fungi which discolor and destroy wood (Basidiomycetes), and against slime organisms and algae.

Microorganisms of the following genera may be mentioned as examples:
Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aurebasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Depending on their particular physical and/or chemical properties, the active compounds can be converted into the customary formulations, such as solutions, emulsions, suspensions, powders, foams, pastes, granules, aerosols, very fine capsules in polymeric substances and in coating compositions for seed, as well as ULV cold-mist and warm-mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

In plant protection, the formulations in general contain between 0.1 and 95 per cent by weight of active compound, preferably between 0.5 and 90%.

When used in plant protection, the active compounds according to the invention can be present in the formulations as a mixture with other known active compounds, such as fungicides, insecticides, acaricides and herbicides, as well as in mixtures with fertilizers and growth regulators.

When used in plant protection, the active compounds can be used as such or in the form of their formulations or the use forms prepared therefrom; such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a relatively wide range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The microbicidal agents used for the protection of industrial materials contain the active compounds in general in an amount of from 1 to 95% by weight, preferably from 10 to 75% by weight.

When used in the protection of materials, the use concentrations of active compounds according to the invention depend on the nature and the occurrence of the microorganisms to be combated, and on the composition of the material to be protected. The optimum application amount can determined by a series of tests. In general, the application concentrations are in the range of from 0.001 to 5% by weight, preferably from 0.05 to 1.0% by weight, based on the material to be protected.

When used in the protection of materials, too, the active compounds according to the invention can be applied in a mixture with other known active compounds.

The following active compounds may be mentioned by way of example: benzyl alcohol mono(poly)hemiformal and other formaldehyde-releasing compounds, benzimidazolylmethylcarbamate, tetramethylthiuram disulphide, zinc salts of dialkyl dithiocarbamates, 2,4,5,6-tetrachloroisophthalonitrile, thiazolylbenzimidazole, mercaptobenzothiazole, 2-thiocyanatomethylthiobenzothiazole, methylene bisthiocyanate, phenol derivatives such as 2-phenylphenol, (2,2'-dihydroxy-5,5'-dichloro)-diphenylmethane and 3-methyl-4-chloro-phenol, organo-tin compounds, and N-trihalogenomethylthio compounds such as folpet, fluorfolpet or dichlofluanid.

The preparation and the use of the active compounds according to the invention are illustrated by the examples which follow.

PREPARATION EXAMPLES

Example 1

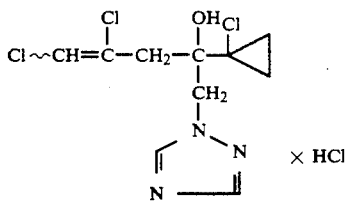

225.5 g (1 mol) of 4-(1-chlorocyclopropyl)-4-hydroxy-5-(1,2,4,-triazol-1-yl)-pent-1-yne in 1.8 liters of absolute methylene chloride are treated at 0° C. first with 5 ml of a 1N solution of hydrogen chloride in ether and then with 1.05 liters of a 1N solution of chlorine in methylene chloride. After the mixture has been stirred for 4 hours at 20° C., another 0.1 mol of the chlorine solution are added. After the mixture has been stirred for a further 2 hours, 360 ml (1 mol) of a solution of hydrogen chloride in ether is added dropwise, with cooling, during which process a salt precipitates.

The reaction mixture is allowed to stand for 16 hours at room temperature and then subjected to filtration with suction. The organic phase which remains is concentrated by stripping off the solvent under reduced pressure. In this manner, 210 g (0.63 mol, 63%) of 4-(1-chlorocyclopropyl)-1,2-dichloro-4-hydroxy-5-(1,2,4-triazol-1-yl)-pent-1-ene hydrochloride are obtained in the form of a solid of melting point 171°–173° C.

NMR (CDCl$_3$): δ=0.6 (m, 2H); 0.9 (m, 1H); 1.25 (m, 1H); 3.2 (AB, 2H); 4.9 (AB, 2H); 6.4 (s, 1H); 6.7 (OH and NH); 8.45 (s, 1H); 9.8 (s, 1H)

Example 2

Into a solution of 5 g (24 mmol) of 4-tert.-butyl-5-(1,2,4-triazol-1-yl)-pent-1-yn-4-ol in 30 ml of dichloromethane there are slowly added dropwise at 0° C. 2.4 g (24 mmol) of concentrated sulphuric acid, with stirring. After this, a solution of 4 g (25 mmol) of bromine in 50 ml of dichloromethane is added dropwise with stirring and exposure to light. The temperature of the reaction mixture is allowed to rise to room temperature, and the mixture is stirred at room temperature for one more hour. The reaction mixture is extracted by shaking twice with aqueous sodium carbonate solution and twice with water, then dried over sodium sulphate and concentrated by stripping off the volatile portions under reduced pressure. In this manner, 7.7 g (87% of theory) of 4-t-butyl-1,2-dibromo-5-(1,2,4-triazol-1-yl)-pent-1-en-4-ol are obtained in the form of a solid with melting point 81° C.

Example 3

Into a solution of 5 g (26 mmol) of 4-(1,2,4-triazol-1-yl-methyl)-hepta-1,6-dien-4-ol in 50 ml of dichloromethane there are slowly added dropwise at 0° C. 2.55 g (26 mmol) of concentrated sulphuric acid, with stirring. At the same temperature, a solution of 8.5 g (53 mmol) of bromine in 20 ml of dichloromethane is then added dropwise with stirring and exposure to light. The temperature of the reaction mixture is allowed to rise to room temperature, and stirring is continued for one hour at room temperature. The reaction mixture is extracted by shaking twice with aqueous sodium carbonate solution and twice with water, then dried over sodium sulphate and evaporated under reduced pressure. The residue which remains is chromatographed on silica gel using a mixture of cyclohexane/dichloromethane 1:1 as the eluent. In this manner, 7.8 g (58% of theory) of 1,2,6,7-tetrabromo-4-(1,2,4-triazol-1-yl-methyl)-hepta-1,6-dien-4-ol are obtained in the form of a solid of melting point 100° C.

Example 4

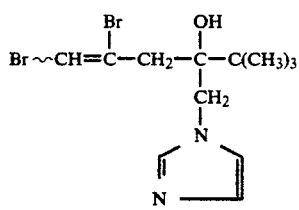

Into a solution of 3 g (14.6 mmol) of 4-(tert.-butyl-5-(imidazol-1-yl)-pent-1-yn-4-ol in 20 ml of dichloromethane there are slowly added dropwise at 0° C. 1.5 g (15 mmol) of concentrated sulphuric acid, with stirring. A solution of 2.5 g (15.6 mmol) of bromine in 20 ml of dichloromethane is then added dropwise with stirring and exposure to light. The temperature of the reaction mixture is allowed to rise to room temperature, and stirring is continued for one hour at room temperature. The reaction mixture is extracted by shaking twice with aqueous sodium carbonate solution and twice with water, then dried over sodium sulphate and concentrated under reduced pressure. In this manner, 4.2 g (77% of theory) of 4-t-butyl-1,2-dibromo-5-(imidazol-1-yl)pent-1-en-4-ol are obtained.

$^1$H NMR (200 MHz, CDCl$_3$): d = 1.02 (s, 9H), 2.79 (d, 1H), 3.14 (d, 1H), 4.07 (d, 1H), 4.22 (d, 1H), 6.61 (s, 1H), 7.03–7.13 (m, 2H), 7.67 (s, 1H) ppm.

Example 5

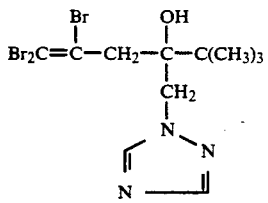

Into a solution of 2 g (7 mmol) of 1-bromo-4-tert.-butyl-5-(1,2,4-triazol-1-yl)-pent-1-yn-4-ol in 20 ml of dichloromethane there are slowly added dropwise at 0° C. 0.7 g (7 mmol) of concentrated sulphuric acid, with stirring. At the same temperature, a solution of 1.3 g (8 mmol) of bromine in 10 ml of dichloromethane is then added dropwise with stirring and exposure to light. The temperature of the reaction mixture is allowed to rise to room temperature, and stirring is continued for two hours at room temperature. The reaction mixture is rendered alkaline by adding aqueous sodium carbonate solution. The organic phase is separated off, washed with water, dried over sodium sulphate and concentrated under reduced pressure. In this manner, 3.1 g (99% of theory) of 4-t-butyl-5-(1,2,4-triazol-1-yl)-1,1,2-tribromopent-1-en-4-ol are obtained in the form of an oily product.

$^1$H NMR (200 MHz, CDCl$_3$): d = 0.96 (s, 9H), 2.87 (d, 1H), 3.43 (d, 1H), 4.3 (broad), 4.46 (s, 2H), 8.0 (s, 1H), 8.28 (s, 1H) ppm.

Preparation of the Starting Compound

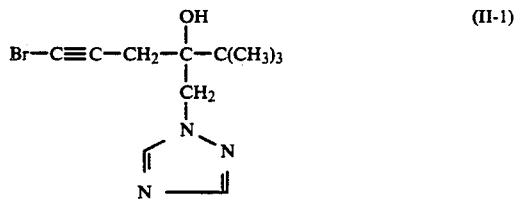

7.7 g (48 mmol) of bromine are added dropwise at temperatures between 0° C. and 5° C. to a solution of 7.2 g (0.13 mol) of potassium hydroxide in 20 ml of water, with stirring. This solution is transferred into a dropping funnel and added dropwise under a nitrogen atmosphere with stirring at room temperature to a solution of 5 g (24 mmol) of 4-tert.-butyl-5(1,2,4-trizol-1-yl)-pent-1-yn-4-ol in 20 ml of tetrahydrofuan. The reaction mixture is allowed to react for 3 hours at 25 to 30° C. and is subsequently poured into ice-water. The mixture formed is extracted with ethyl acetate. The combined organic phases are dried over sodium sulphate and concentrated by stripping off the solvent under reduced pressure. In this manner, 6.3 g (91% of theory) of 1-bromo-4-t-butyl-5-(1,2,4-trizol-1-yl)-pent-1-yn-4-ol are obtained in the form of an oily product.

$^1$H NMR (200 MHz, CDCl$_3$): d = 1.08 (s, 9H), 2.13 (d, 1H), 2.57 (d, 1H), 3.78 (broad, 1H), 4.33 (d, 1H), 4.58 (d, 1H), 8.02 (s, 1H),1 8.44 (s, 1H) ppm.

The substances of the formula

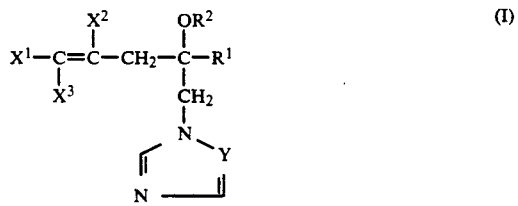

listed in Table 2 below are also prepared by the above-mentioned methods.

TABLE 2

| Example No. | Comp. No. | X$^1$ | X$^2$ | X$^3$ | R$^1$ | R$^2$ | Y | Melting point(°C.) or $^1$H-NMR(CDCl$_3$, 200 MHz) |
|---|---|---|---|---|---|---|---|---|
| 6 | I-6 | Br | Br | Br | ⟨⟩—Cl | H | N | δ = 0.34–0.57(m, 2H), 0.77–0.9(m, 1H), 1.02–1.18(m, 1H), 3.21(d, 1H), 3.59 (d, 1H), 4.48 (broad) and 4.48 (d, 2H), 4.95(d, 1H), 8.02 (2, 1H), 8.39(s, 1H)ppm |

TABLE 2-continued

| Example No. | Comp. No. | X¹ | X² | X³ | R¹ | R² | Y | Melting point(°C.) or ¹H-NMR(CDCl₃, 200 MHz) |
|---|---|---|---|---|---|---|---|---|
| 7 | I-7 | Br | Br | H | 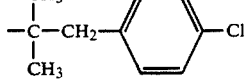 | H | N | δ = 0.83(s, 3H), 0.88(s, 3H), 2.65(d, 1H), 2.75(d, 1H), 2.92(d, 1H), 3.32(d, 1H), 4.49(d, 1H), 4.52(d, 1H), 6.57(s, 1H), 7.07(d, 2H), 7.28(d, 2H), 8.0(s, 1H), 8.26((s, 1H)ppm |
| 8 | I-8 | Br | Br | H | 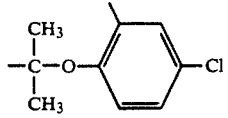 | H | N | δ = 1.25(s, 3H), 1.32(s, 3H), 3.2 (d, 1H), 3.4(d, 1H), 4.66 (d, 1H), 4.75(d, 1H), 6.65 (s, 1H), 7.05(d, 1H), 7.17 (dd, 1H), 7.4(d, 1H), 7.93 (s, 1H), 8.35(s, 1H) ppm |
| 9 | I-9 | Br | Br | H | 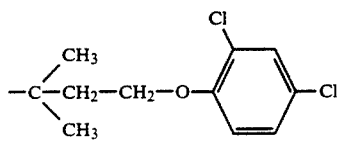 | H | N | δ = 1.02(s, 3H) 1.12(s, 3H), 2.0(m, 2H), 2.86(d, 1H), 3.32(d, 1H), 4.15(m, 2H), 4.48(s, 2H), 6.53(s, 1H), 6.87(d, 1H), 7.18(dd, 1H), 7.38(d, 1H), 7.98(s, 1H), 8.22((s, 1H)ppm |
| 10 | I-10 | Br | Br | H | 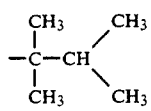 | H | N | δ = 0.78(s, 3H), 0.95(d, 3H), 0.97 (s, 3H), 1.04(d, 3H), 1.87 (hept, 1H), 2.87(d, 1H), 3.29 (d, 1H), 4.28(s, 1H), 4.41 (d, 1H), 4.51(d, 1H), 6.52 (s, 1H), 7.96(s, 1H), 8.21 (s, 1H) ppm. |
| 11 | I-11 | Br | Br | H | 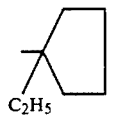 | H | N | δ = 0.95(t, 3H) 1.4–2.0(m, 8H), 2.86(d, 1H), 3.27 (d, 1H), 4.25(1H), 4.48(s, 1H), 4.49 (s, 1H), 6.54(s, 1H), 8.05 (s, 1H), 8.65(s, 1H) ppm. |
| 12 | I-12 | Br | Br | H |  | H | N | δ = 0.32–0.54(m, 2H), 0.78–0.90(m, 1H), 1.03–1.17(m, 1H), 3.06(d, 1H), 3.55 (m, 1H), 4.44(d, 1H), 4.93 (d, 1H), 6.87(s, 1H), 8.04 (s, 1H), 8.32(s, 1H) ppm. |
| 13 | I-13 | Br | Br | H | 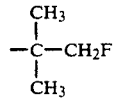 | H | N | δ = 0.91–2.00(m, 6H), 2.83(d, 1H), 3.26 (d, 1H), 4.2–5.2 (m, 5H), 6.54(s, 1H), 7.96 (s, 1H), 8.22(s, 1H) ppm. |
| 14 | I-14 | Br | Br | H | 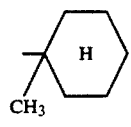 | H | N | δ = 1.04(s, 3H), 1.1–1.7(m, 10H), 2.82(d, 1H), 3.22 (d, 1H), 4.41(d, H), 4.51 (d, 1H), 6.52(s, 1H), 8.02 (s, 1H), 8.33(s, 1H) ppm. |
| 15 | I-15 | Br | Br | H | 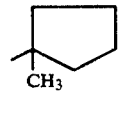 | H | N | m.p. 120° C. |
| 16 | I-16 | Cl | Cl | H | —C(CH₃)₃ | H | N | δ = 6.2(s, —CCl=CHCl) |
| 17 | I-17 | Cl | Cl | H | 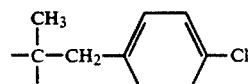 | H | N | δ = 6.25(s, —CCl=CHCl) |
| 18 | I-18 | Cl | Cl | H | 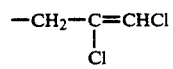 | H | N | δ = 6.45(s, —CCl=CHCl) |

TABLE 2-continued

| Example No. | Comp. No. | X¹ | X² | X³ | R¹ | R² | Y | Melting point(°C.) or $^1$H-NMR(CDCl$_3$, 200 MHz) |
|---|---|---|---|---|---|---|---|---|
| 19 | I-19 | Cl | Cl | H | —CH$_2$—C≡CH | H | N | δ = 6.4(s, —CCl=CHCl) |
| 20 | I-20 | Cl | Cl | H |  | H | N | m.p. 88–89° |
| 21 | I-21 | Cl | Cl | H | 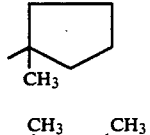 | H | N | (x HCl) m.p. 49–52° |
| 22 | I-22 | Cl | Cl | H | 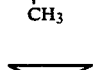 | H | N | δ = 6.45(s, —CCl=CHCl) |

In the use examples which follow the compounds of the formulae listed below were employed as comparison substances:

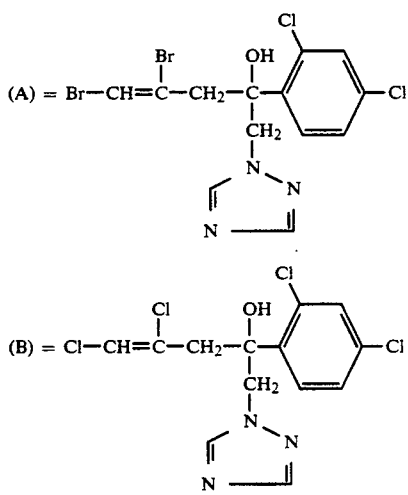

(Disclosed in EP-OS (European Published Specification) 0,097,425)

Example A

Erysiphe Test (Barley)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of mildew pustules.

Evaluation is carried out 7 days after the inoculation.

In this test, a very good activity is shown by the substances according to the invention (I-6), (I-10) and (I-13).

Example B

Erysiphe Test (Wheat)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. tritici.

The plants are placed in a greenhouse at a temperature of about 20° C. and a relative atmospheric humidity of about 80%, in order to promote the development of mildew pustules.

Evaluation is carried out 7 days after the inoculation.

In this test, a very good activity is shown by the compound (I-10) according to the invention.

Example C

*Leptosphaeria nodorum* Test (Wheat)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a very good activity is shown by compound (I-13) according to the invention.

Example D

*Pyrenophora teres* Test (Barley)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres*. The plants remain for 48 hours in an incubation cabin at 20° C. and 100% relative atmospheric humidity.

The plants are placed in a greenhouse at a temperature of about 20° C. and a relative atmospheric humidity of about 80%.

Evaluation is effected 7 days after the inoculation.

In this test, a very good activity is shown by compounds (I-6) and (I-10) according to the invention.

Example E

*Fusarium nivale* Test (Rye)/Seed Treatment

The active compounds are applied as dry seed-dressing agents. They are prepared by extending the particular active compound with ground rock to give a finely pulverulent mixture which guarantees uniform distribution on the seed surface.

For seed-dressing, the infected seed and the seed-dressing agent are shaken for 3 minutes in a sealed glass flask.

Rye is sown in two 100-grain batches in a standard soil at a depth of 1 cm and grown in the greenhouse at a temperature of about 10° C. and a relative atmospheric humidity of about 95% in seed boxes which are exposed to the light for 15 hours/day.

About 3 weeks after sowing, the plants are evaluated for snow-mold symptoms.

In this test, better activity than comparison substance (A) is shown by the compounds according to the invention (I-1), (I-2), (I-3), (I-5), (I-6), (I-8), (I-10), (I-12, (I-13) and (I-21).

Example F

Erysiphe Test (Barley)/Seed Treatment

The active compounds are applied as dry seed-dressing agents. They are prepared by extending the particular active compound with ground rock to give a finely pulverulent mixture which guarantees uniform distribution on the seed surface.

For seed-dressing, the infected seed and the seed-dressing agent are shaken for 3 minutes in a sealed glass flask.

The barley is sown in 3 batches of 12 grains in standard soil at a depth of 2 cm. 7 days after sowing, when the plants have unfolded their first leaf, they are dusted with spores of *Erysiphe graminis* f.sp. hordei.

The plants are placed in a greenhouse at a temperature of about 20° C. and a relative atmospheric humidity of about 80%, in order to promote the development of mildew pustules.

The evaluation takes place 7 days after the inoculation.

In this test, better activity than comparison substance (B) is shown by the compounds according to the invention (I-1), (I-3), (I-6), (I-12 and (I-13).

Example G

Pyricularia Test (Rice)/Protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

The evaluation takes place 4 days after the inoculation.

In this test, a better activity than by comparison substance (A) is shown by the substances according to the invention (I-2), (I-6), (I-12), (I-21) and (I-22).

Example H

Pyricularia Test (Rice)/Systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a better activity than by comparison substance (B) is shown by the compounds according to the invention (I-2) and (I-22).

Example I

Pellicularia Test (Rice)/Protective

Solvent: 12.5 parts by weight of acetone
Emulsifier: 0.3 partsby weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for activity, young rice plants in the 3 to 4 leaf stage are sprayed until dripping wet. The plants remain in a greenhouse until they have dried off. The plants are then inoculated with *Pellicularia sasakii* and are set up at 25° C. and 100% relative atmospheric humidity.

The evaluation of the disease infestation is carried out 5 to 8 days after the inoculation.

In this test, a better activity than by comparison substance (B) is shown by the substances according to the invention (I-2), (I-6), (I-12), (I-21) and (I-22).

Example K

*Fusarium culmorum* Test/Wheat/Protective

Solvent: 100 parts by weight of acetone
Emulsifier: 4.5 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, plants aged 7 days are sprayed with the preparation of active compound until dripping wet. After 24 hours, the plants are sprayed with *Fusarium culmorum* conidia which are suspended in a 2.4% strength potato dextrose broth (Difco). Immediately beforehand, the leaves are damaged by piercing with a needle. Until the plants are evaluated, they remain for 7 days in a translucent incubation chamber in which the temperature is 27° C. during the day and 21° C. during the night and in which the atmospheric humidity is 100%.

In this test, a very good activity is shown by the compounds according to the invention (I-2), (I-5), (I-6), (I-7), (I-10), (I-11), (I-12) and (I-13).

Example L

*Gibberella zeae* (= *Fusarium graminearum*) Test/Barley/Protective

Solvent: 100 parts by weight of acetone
Emulsifier: 4.5 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, plants aged about 7 days are sprayed with the preparation of active compound until dripping wet. After 24 hours, the plants are sprayed with *Gibberella zeae* conidia which are suspended in a 2.4% strength potato dextrose broth (Difco). Immediately beforehand, the leaves are damaged by piercing with a needle. Until the plants are evaluated, they remain for 7 days in a translucent incubation chamber in which the temperature is 27° C. during the day and 21° C. during the night and in which the atmospheric humidity is 100%.

In this test, a very good activity is shown by the compounds according to the invention (I-2), (I-5), (I-6), (I-7), (I-10), (I-11), (I-12), (I-13) and (I-16).

Example M

*Fusarium nivale* Test/Wheat/Protective

Solvent: 100 parts by weight of acetone
Emulsifier: 4.5 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, plants aged 7 days are sprayed with the preparation of active compound until dripping wet. After 24 hours, the plants are sprayed with *Fusarium nivale* conidia which are suspended in a 2.4% strength potato dextrose broth (Difco). Immediately beforehand, the leaves are damaged by piercing with a needle. Until the plants are evaluated, they remain for 5–6 days in a translucent incubation chamber in which the temperature is 20° C. during the day and 15° C. during the night and in which the atmospheric humidity is 100%.

In this test, a very good activity is shown by the compounds according to the invention (I-2), (I-5), (I-6), (I-7), (I-10), (I-11), (I-12) and (I-13).

Example N

*Pseudocercosporella herpotrichoides* Test (Wheat)Protective

Solvent: 100 parts by weight of dimethylformamide
Emulsifier: 0.25 parts by weight of alkylaryl polyglycol ether To product a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the sprayed coating has dried on, the plants are inoculated at the stem base with spores of *Pseudocercosporella herpotrichoides.*

The plants are placed in a greenhouse at a temperature of about 10° C. and a relative atmospheric humidity of about 80%.

The evaluation takes place 21 days after the inoculation.

In this test, a better activity than by comparison substances (A) and (B) is shown by the substances according to the invention (I-1), (I-2) and (I-10).

Example O

Botrytis Test (Bean)/Protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened, humid chamber at 20° C. 3 days after the inoculation, the size of the infected spots on the leaves is evaluated.

In this test, a very good activity is shown by the compounds according to the invention (I-1), (I-2), (I-6), (I-7), (I-10), and (I-12).

Example P

Venturia Test (Apple)/Protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a very good activity is shown by the compounds according to the invention (I-5), (I-6), (I-7), (I-9), (I-10), and (I-16).

It will be understood that the specification and examples are illustrative but not limitative of the present invention and that other embodiments within the spirit and scope of the invention will suggest themselves to those skilled in the art.

We claim:

1. A halogenoallyl-azolyl compound of the formula

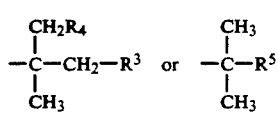

in which

R$^1$ represents allyl which is monosubstituted to trisubstituted by fluorine, chlorine and/or bromine, or represents propargyl or represents cycloalkyl having 3 to 6 carbon atoms, each of these cycloalkyl radicals being monosubstituted or disubstituted by methyl, ethyl, fluorine, chlorine or bromine, or R$^1$ represents a radical of the formula

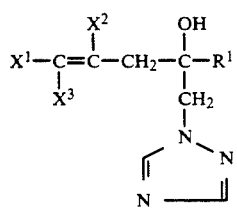

where

R$^3$ represents hydrogen, fluorine, chlorine, phenyl which is optionally monosubstituted or disubstituted by identical or different substituents, the substituents being fluorine or chlorine, or phenoxy which is optionally monosubstituted or disubstituted by identical or different substituents, the substituents being fluorine or chlorine, or represents phenoxymethyl which is optionally monosubstituted or disubstituted by identical or different substituents, the substituents being fluorine or chlorine, R$^4$ represents hydrogen, fluorine or chlorine, R$^5$ represents iso-propyl, or phenyl which is optionally monosubstituted or disubstituted by identical or different substituents, the substituents being fluorine or chlorine, or represents phenoxy which is optionally monosubstituted or disubstituted by identical or different substituents, the substituents being fluorine or chlorine, X$^1$ represents chlorine or bromine, X$^2$ represents chlorine or bromine and X$^3$ represents hydrogen, chlorine or bromine, or an addition product thereof with an acid or metal salt.

2. A compound according to claim 1, wherein such compound is 4-(1-chlorocyclopropyl)-1,2-dichloro-4-hydroxy-5-(1,2,4-triazol-1-yl)-pent-1-ene of the formula

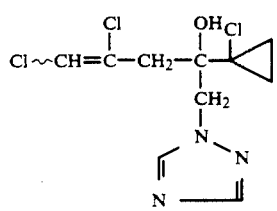

or an addition product thereof with an acid or metal salt.

3. A compound according to claim 1, wherein such compound is 4-t-butyl-1,2-dibromo-5-(1,2,4-triazol-1-yl)-pent-1-en-4-ol of the formula

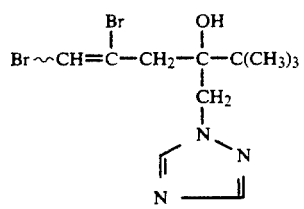

or an addition product thereof with an acid or metal salt.

4. A compound according to claim 1, wherein such compound is 4-t-butyl-5-(1,2,4-triazol-1-yl)-1,1,2-tribromopent-1-en-4-ol of the formula

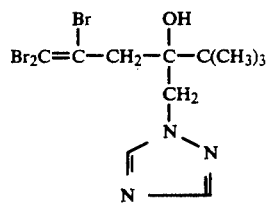

or an addition product thereof with an acid or metal salt.

5. A compound according to claim 1, wherein such compound is 4-(1-chlorocyclopropyl)-5-(1,2,4-triazol-1-yl)-1,1,2-tribromopent-1-en-4-ol of the formula

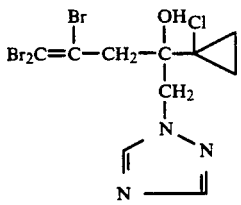

or an addition product thereof with an acid or metal salt.

6. A microbicidal composition comprising a microbicidally effective amount of a compound or addition product thereof according to claim 1 and an inert diluent.

7. A method of combating microbes which comprises applying to such microbes or to a locus from which it is desired to exclude such microbes a microbicidally effective amount of a compound or addition product thereof according to claim 1.

8. The method according to claim 7, wherein such compound is 4-(1-chlorocyclopropyl)-1,2-dichloro-4-hydroxy-5-(1,2,4-triazol-1-yl)-pent-1-ene, 4-t-butyl-1,2-dibromo-5-(1,2,4-triazol-1-yl)-ent-1-en-4-ol, 4-t-butyl-5-(1,2,4-triazol-1yl)-1,1,2-tribromopent-1-en-4-ol or 4-(1-chlorocyclopropyl)-5-(1,2,4-triazol-1-yl)-1,1,2-tribromopent-1-en-4-ol, or an addition product thereof with an acid or metal salt.

* * * * *

UNITED STATES PATENT AND TRADEMARK OFFICE
CERTIFICATE OF CORRECTION

PATENT NO. : 5,122,532
DATED : June 16, 1992
INVENTOR(S) : Jautelat, et.a l.

It is certified that error appears in the above-indentified patent and that said Letters Patent is hereby corrected as shown below:

On the Title page, item [57], Abstract: col. 2, lines 17-18 delete " or phenoxy which is optionally substituted by halogen" (second occurrence).

Signed and Sealed this

First Day of February, 1994

Attest:

BRUCE LEHMAN

Attesting Officer    Commissioner of Patents and Trademarks